United States Patent
Zhou et al.

(10) Patent No.: US 8,598,301 B2
(45) Date of Patent: Dec. 3, 2013

(54) COPOLYMER CONTAINING FLUORENYLPORPHYRIN-ANTHRACENE, PREPARATION METHOD AND APPLICATION THEREOF

(75) Inventors: Mingjie Zhou, Guangdong (CN); Jie Huang, Guangdong (CN); Yijin Liu, Guangdong (CN)

(73) Assignee: Ocean's King Lighting Science & Technology Co., Ltd., Guangdong (CN)

( * ) Notice: Subject to any disclaimer, the term of this patent is extended or adjusted under 35 U.S.C. 154(b) by 0 days.

(21) Appl. No.: 13/575,684

(22) PCT Filed: Jan. 30, 2010

(86) PCT No.: PCT/CN2010/070435
§ 371 (c)(1),
(2), (4) Date: Jul. 27, 2012

(87) PCT Pub. No.: WO2011/091607
PCT Pub. Date: Aug. 4, 2011

(65) Prior Publication Data
US 2012/0302717 A1    Nov. 29, 2012

(51) Int. Cl.
*C08G 65/38*    (2006.01)
(52) U.S. Cl.
USPC ............ 528/216; 528/94; 528/118; 528/117; 528/54; 528/64; 528/171; 528/239
(58) Field of Classification Search
USPC ................. 528/216, 94, 117, 118, 54, 62, 64; 526/171, 239
See application file for complete search history.

(56) References Cited

U.S. PATENT DOCUMENTS

| | | |
|---|---|---|
| 6,420,648 B1 | 7/2002 | Lindsey |
| 2007/0043222 A1 | 2/2007 | Yoshimoto et al. |
| 2009/0314660 A1 | 12/2009 | Canonne et al. |

FOREIGN PATENT DOCUMENTS

| | | |
|---|---|---|
| CN | 1459127 A | 11/2003 |
| CN | 1887033 A | 12/2006 |
| EP | 1389626 A1 | 2/2004 |
| WO | 2007/051947 A1 | 5/2007 |

OTHER PUBLICATIONS

Li et al. (Macromolecules 2006, 39, 456-461).*
Li, et al.; "Porphyrins With Four Monodisperse Oligofluorene Arms as Efficient Red Light-Emitting Materials"; JACS, 2004, vol. 126, pp. 3430-3431.
Communication from the European Patent Office regarding a counterpart foreign application dated May 15, 2013.
Communication from the Chinese Patent Office regarding a counterpart foreign application dated Jun. 5, 2013.

* cited by examiner

*Primary Examiner* — Shane Fang
(74) *Attorney, Agent, or Firm* — Rosenberg, Klein & Lee

(57) ABSTRACT

A copolymer containing fluorenylporphyrin-anthracene is disclosed, which comprises a polymer represented by formula (1), in which $R_1$, $R_2$, $R_3$ and $R_4$, which may be identical or different, are $C_1$-$C_{16}$ alkyl, and n is an integer of 1 to 100. A preparation method of the copolymer containing fluorenylporphyrin-anthracene and the application thereof in manufacture of solar cell devices, organic field-effect transistors, organic electroluminescent devices, organic optical storage device, organic nonlinear materials or organic laser devices are also disclosed.

13 Claims, 4 Drawing Sheets

COPOLYMER CONTAINING FLUORENYLPORPHYRIN-ANTHRACENE, PREPARATION METHOD AND APPLICATION THEREOF

FIELD OF THE INVENTION

The present disclosure relates to organic materials, and more particularly relates to a copolymer containing fluorenylporphyrin-anthracene, preparation method thereof, and applications thereof.

BACKGROUND OF THE INVENTION

Today's world economy is mainly based on fossil energy, such as coal, oil and natural gas. However, these non-renewable fossil energy are becoming exhausted. Since the beginning of the 21st century, global energy issues, the consequent environmental pollution and global warming become increasingly apparent and intense. Solar energy has numerous advantages such as the broad and widespread distribution, large resource quantity, no pollution, clean, safety and convenient access, therefore it is considered to be one of the most promising renewable sources of energy.

To take full advantage of the solar energy radiated from the sun, people continue to develop new materials to absorb sunlight, in which inorganic semiconductor materials, such as silicon cells used on the ground, has gained broader development and application. However, due to their complex process and high cost, the application of the silicon cells has been strictly limited. In order to reduce costs and expand the application scope, people have been looking for new alternative semiconductor materials for a long period of time.

In recent years, organic materials have gradually gained widespread interest. For example, after the report of photo-induced electron transfer phenomena between conjugated polymers and $C_{60}$ by N. S. Sariciftci in 1992, people have put lots of research on conjugated polymer used in the solar cell, and have achieved rapid development. Solar cells directly transform solar energy into electric energy, which is an effective method of using solar energy.

Organic solar cell is a new type of solar cell. Compared with the disadvantages of the inorganic semiconductor materials such as limited sources, high prices, toxicity, complicated preparation process, high cost, the organic solar cell has some advantages such as wide range of materials, structural diversity and manageability, low cost, safety and environmental protection, simple production process, light weight of product, flexible preparation for large area, etc., thus it has important developing and applicable prospects and can be widely used in the fields of architecture, illumination and power generation. However, photoelectric conversion efficiency of organic solar cells is much lower than that of inorganic solar cells for now. Therefore, the development of new organic materials is of great significance for improving the efficiencies of organic solar cells and other semiconductor devices or optoelectronic devices.

SUMMARY OF THE INVENTION

In one aspect of the present disclosure, a copolymer containing fluorenylporphyrin-anthracene is provided having a wide spectral response and good stability, and a preparation method for the copolymer containing fluorenylporphyrin-anthracene is also provided having a simple synthetic route and a low cost.

In another aspect of the present disclosure, a method for the applications of the copolymer containing fluorenylporphyrin-anthracene in the manufacture of solar cell devices, organic field-effect transistors, organic electroluminescent devices, organic optical storage devices, organic nonlinear materials or organic laser devices is provided.

A copolymer containing fluorenylporphyrin-anthracene, comprising a polymer represented by formula (1):

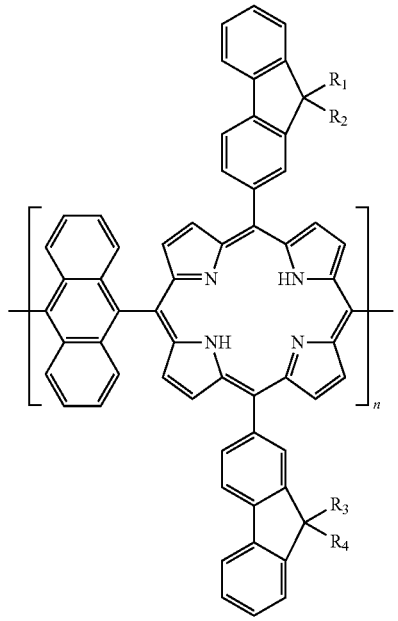

(1)

wherein $R_1$, $R_2$, $R_3$ and $R_4$, which may be identical or different, are $C_1$-$C_{16}$ alkyl, and n is an integer of 1 to 100.

A preparation method of a copolymer containing fluorenylporphyrin-anthracene, comprising the steps of: providing compounds A, B, C, and D represented by formulas:

A:

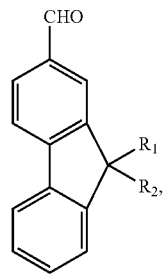

B:

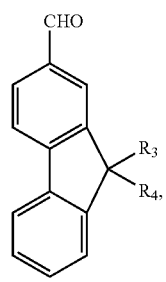

C:

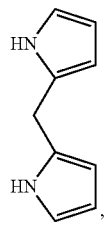

D:

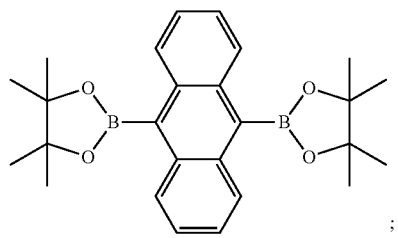

wherein $R_1$, $R_2$, $R_3$ and $R_4$, which may be identical or different, are $C_1$-$C_{16}$ alkyl; performing polycondensation oxidation reaction with compounds A, B, and C in a system containing a solvent, a catalyst and an oxidant to produce a fluorenyl porphyrin compound;
performing bromide substitution reaction with the fluorenyl porphyrin compound in a system containing a solvent and a catalyst to produce a dibromo substituted fluorenyl porphyrin compound; and
Suzuki polymerizing the dibromo substituted fluorenyl porphyrin compound and the compound D in the presence of a catalyst, a solvent, and an alkaline solution to produce a polymer represented by formula (1):

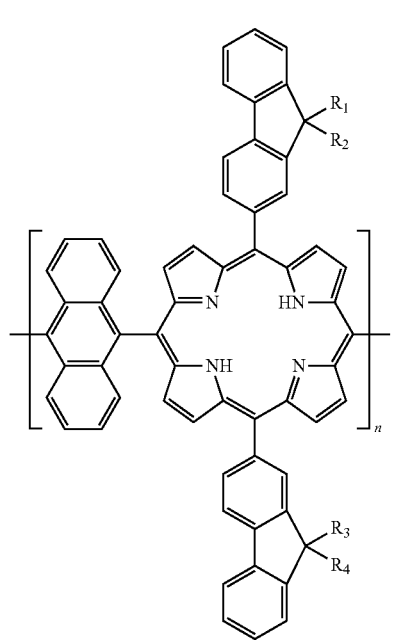

(1)

wherein n is an integer of 1 to 100.

A method for the applications of the copolymer containing fluorenylporphyrin-anthracene in the manufacture of solar cell devices, organic field-effect transistors, organic electroluminescent devices, organic optical storage devices, organic nonlinear materials or organic laser devices.

In the copolymer containing fluorenylporphyrin-anthracene described above, the fluorene or fluorene derivatives have excellent light stability and thermal stability, and have structures for easy modification. Heterocyclic multi-aromatic ring or aromatic heterocyclic molecules can be introduced to increase the density of the skeletal electron cloud of the copolymer containing fluorenylporphyrin-anthracene, so as to narrow the copolymer bandgap. Porphyrin structure can make the copolymer appear a high quantum efficiency of the charge transfer and energy transfer reactions, and an excellent electronic buffer and photoelectromagnetism, a good rigid-flexibility, a better thermal stability and environmental stability. Anthracene has a good stability and good film-forming ability, too, it also possesses a better carrier transport characteristic. Anthracene has a high hole mobility, such that the carrier transport properties and the carrier transport characteristic of the copolymer containing fluorenylporphyrin-anthracene can be improved. When the copolymer containing fluorenylporphyrin-anthracene is applied to solar cell devices, organic field-effect transistors, organic electroluminescent devices, organic optical storage devices, organic nonlinear materials or organic laser devices, the optical or semiconductor-related performance can be improved, and it can reduce the weight of the device, and thus facilitating the large quantities preparation.

BRIEF DESCRIPTION OF THE DRAWINGS

The components in the drawings are not necessarily drawn to scale, the emphasis instead being placed upon clearly illustrating the principles of the present disclosure. Moreover, in the drawings, like reference numerals designate corresponding parts throughout the views.

DETAILED DESCRIPTION

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Figure 1:
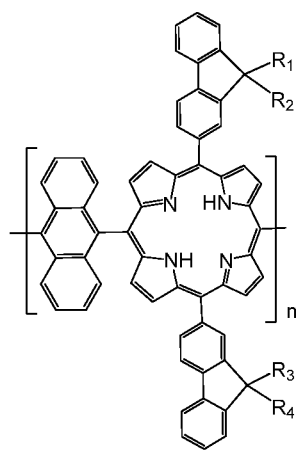
FIG. 1 illustrates a formula of a copolymer containing fluorenylporphyrin-anthracene according to an embodiment of the present disclosure.

Referring to FIG. 1, an embodiment of a copolymer containing fluorenylporphyrin-anthracene is a polymer represented by formula (1):

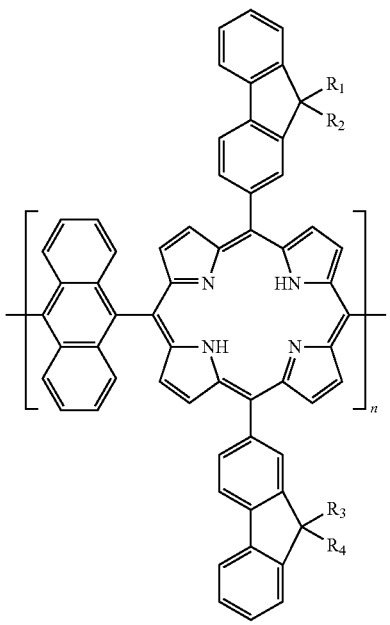

(1)

wherein $R_1$, $R_2$, $R_3$ and $R_4$, which may be identical or different, are $C_1$-$C_{16}$ alkyl, and n is an integer of 1 to 100.

In one embodiment, each monomer of the copolymer containing fluorenylporphyrin-anthracene have two identical fluorene groups containing alkyl, i.e. $R_1$, $R_3$ are identical $C_1$-$C_{16}$ alkyl, and $R_2$, $R_4$ are identical $C_1$-$C_{16}$ alkyl, in other words, $R_1$ and $R_4$ are identical $C_1$-$C_{16}$ alkyl, and $R_2$ and $R_3$ are identical $C_1$-$C_{16}$ alkyl. In this manner, preparation process can be simplified and the cost can be reduced. In addition, containing alkyl can improve the solubility of the copolymer. Preferably, $R_1$, $R_2$, $R_3$, and $R_4$ are identical $C_1$-$C_{16}$ alkyl. The n is preferably an integer of 5 to 50, more preferably 10 to 30. In one embodiment, $R_1$, $R_2$, $R_3$, and $R_4$ are $C_8$ alkyl.

The copolymer containing fluorenylporphyrin-anthracene includes fluorene or fluorene derivatives, porphyrin structure and anthracene structure. The fluorene or fluorene derivatives have excellent light stability and thermal stability, and have structures for easy modification. Heterocyclic multi-aromatic ring or aromatic heterocyclic molecules can be introduced to increase the density of the skeletal electron cloud of the copolymer containing fluorenylporphyrin-anthracene, so as to narrow the copolymer bandgap. Porphyrin structure can make the copolymer appear a high quantum efficiency of the charge transfer and energy transfer reactions, and an excellent electronic buffer and photoelectromagnetism, a good rigid-flexibility, a better thermal stability and environmental stability. Anthracene has a good stability and good film-forming ability, too, it also possesses a better carrier transport characteristic. Anthracene has a high hole mobility, such that the carrier transport properties and the carrier transport characteristic of the copolymer containing fluorenylporphyrin-anthracene can be improved.

The copolymer containing fluorenylporphyrin-anthracene includes a plurality of thiophene rings, and it possesses a modest bandgap, wide spectral response, which is about 300~700 nm bands covering the visible light. It has a good thermal stability and environmental stability and appears an improving optical and electrical properties. In the embodiment of the copolymer containing fluorenylporphyrin-anthracene, $R_1$, $R_2$, $R_3$, and $R_4$ are preferably alkyl chain, e.g. $C_6$, or more than $C_6$ alkyl chain. The dissolution properties of the material is improved since alkyl chain is introduced, such that film processing becomes conducive, and application field is expanded.

Figure 2:
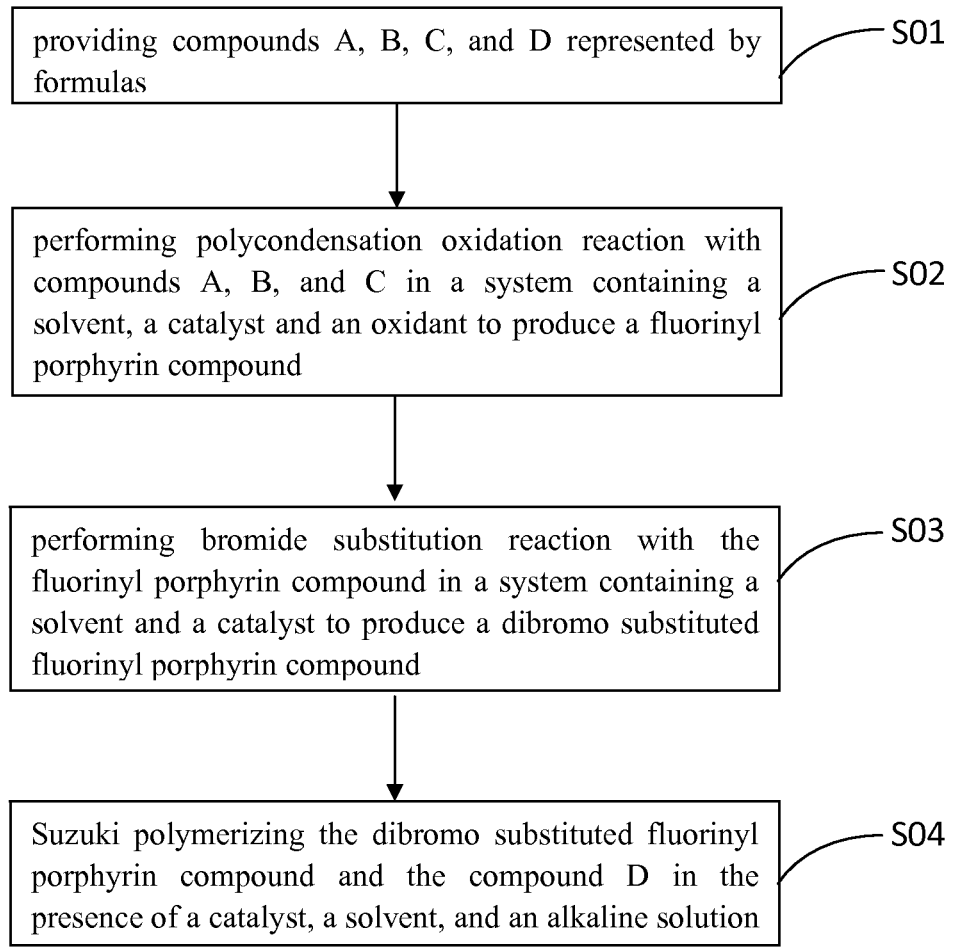
FIG. 2 is a flowchart of an embodiment of a method for preparing a copolymer containing fluorenylporphyrin-anthracene.

Referring to the FIG. 2, a preparation method of the copolymer containing fluorenylporphyrin-anthracene described above includes the following steps:

In step S01, compounds A, B, C, and D represented by formulas are provided:

A:

B:

C:

D:

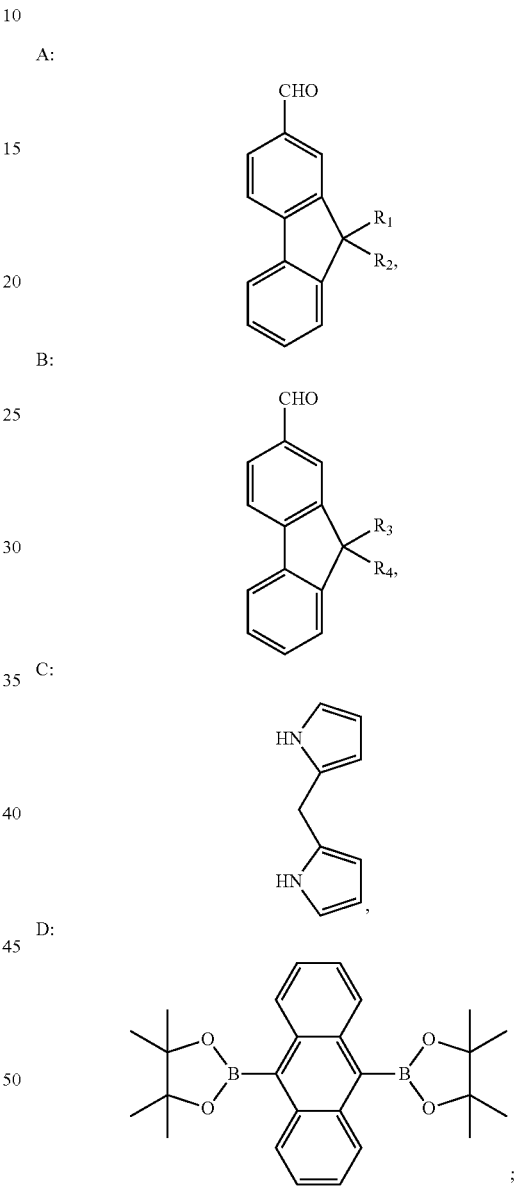

wherein $R_1$, $R_2$, $R_3$ and $R_4$, which may be identical or different, are $C_1$-$C_{16}$ alkyl;

In step S02, compounds A, B, and C are performed with polycondensation oxidation reaction in a system containing a solvent, a catalyst and an oxidant to produce a fluorenyl porphyrin compound.

In step S03, the fluorenyl porphyrin compound is performed with bromide substitution reaction in a system containing a solvent and a catalyst to produce a dibromo substituted fluorenyl porphyrin compound.

In step S04, the dibromo substituted fluorenyl porphyrin compound and the compound D are Suzuki polymerized in the presence of a catalyst, a solvent, and an alkaline solution to produce a polymer represented by formula (1):

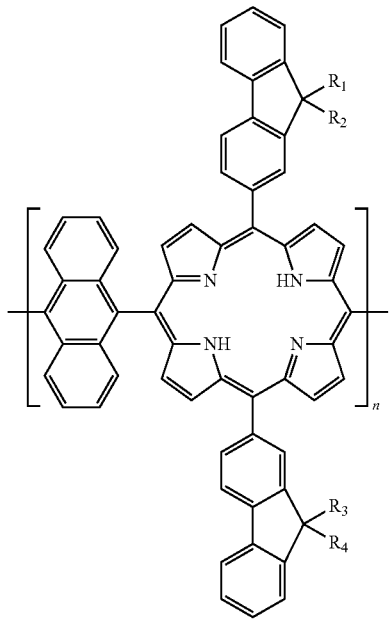

(1)

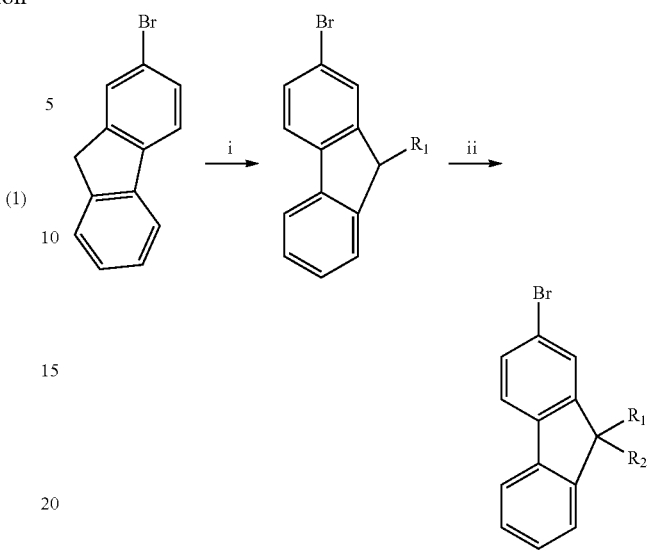

The preparation of the compound 9,9-dialkyl-2-bromo fluorine can be referred to *Macromolecules,* 2002, 35, 3474.

Step two, Bromine hydroformylation reaction was carried out in a system containing alkyl lithium, dimethyl formamide and solvent, as illustrated in the following scheme.

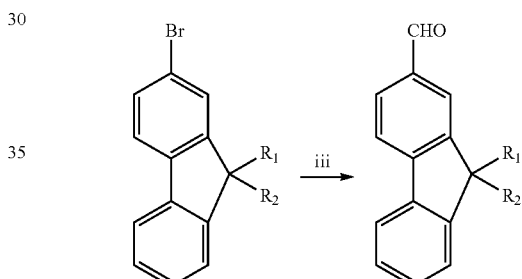

In a specific embodiment, alkyl lithium was N-butyl lithium, and the solvent was tetrahydrofuran. The detailed preparation can be referred to *Macromolecules,* 2006, 39, 456.

The steps of preparation of the compound B was similar to the steps of compound A, except the alkyls of the two bromine alkyls were $R_3$, $R_4$.

2. Preparation of the Compound C

The compound C was obtained by condensation reaction in a system containing formaldehyde, catalyst and pyrrole. The reaction equation was as follows:

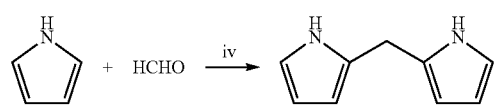

In the step iv, the catalyst may be trifluoroacetic acid or boron trifluoride dimethyl-oxygen complex ($BF_3.(CH_3)_2O$). The pyrrole serves both as solvent and reactant. The detailed preparation of the compound C, namely bipyrrole methane can be referred to Tetrahedron, 1994, 39, 11427.

3. Preparation of the Compound D

Butyl lithium was engaged with boron esters in a substitution reaction, as illustrated in the following scheme.

wherein n is an integer of 1 to 100.

In step S01, the compounds A, B, C, and D can be directly purchased from the market or prepared according to conventional synthesis method. The $R_1$, $R_2$, $R_3$ and $R_4$ of the compounds A, B, C, and D have the same structure as previously described with the copolymer containing fluorenylporphyrin-anthracene. For example, in a preferably embodiment, $R_1$, $R_3$ are identical $C_1$-$C_{16}$ alkyl, and $R_2$, $R_4$ are identical $C_1$-$C_{16}$ alkyl. In this case, the compound A and the compound B have the same structure, thus less raw material can be used, and simplifying the fabrication process and reduce costs, boosting the production yield comparing to a situation in which compounds A, B are different.

In one embodiment, the compounds A, B, C, and D are prepared according to the methods described below.

1. Preparation of Compounds A and B.

The compound A is prepared according to the method including the steps of:

Step one, 2-bromo-fluorene was engaged with bromine alkyl in a substitution reaction in condition of a catalyst and solvent to obtained 9,9-dialkyl-2-bromo-fluorene. The catalyst was tetrabutylammonium bromide or benzyl triethyl ammonium chloride, the solvent was toluene, dimethyl sulfoxide, tetrahydrofuran, etc. The bromine alkyl was two bromine alkyls which has alkyl as $R_1$ and $R_2$, respectively. As illustrated in the following scheme, the reaction takes two steps, e.g. step i and step ii, two bromine alkyls were used in the substitution reaction.

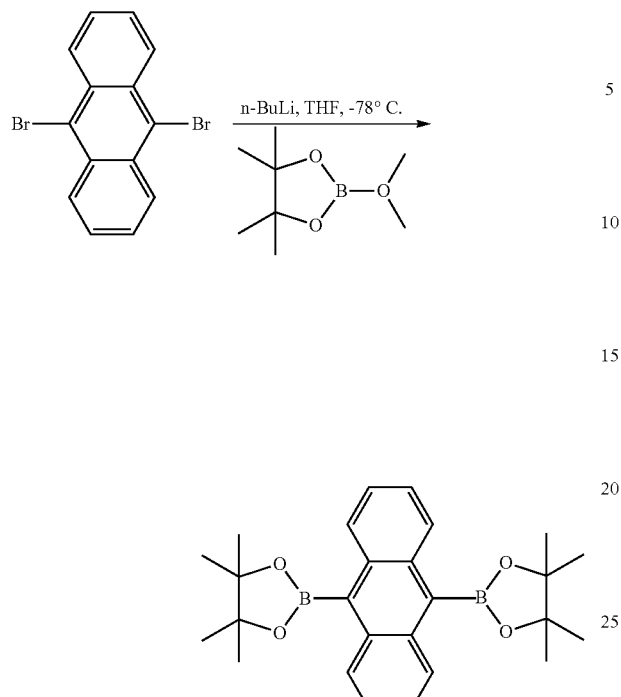

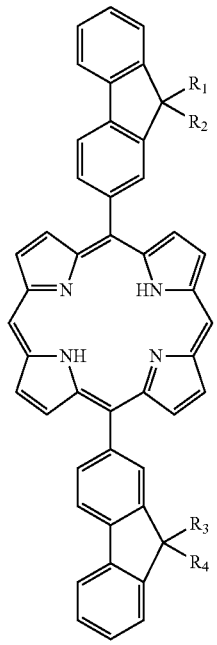

In detail, 9,10-dibromo anthracene was added to a three-neck flask under the protection of $N_2$, then tetrahydrofuran (150 ml) was added, next butyl lithium was slowly injected by a syringe at a temperature −78° C. After the mixture was stirred for 2 hours, 2-isopropoxy-4,4,5,5-tetramethyl-1,3,2-dioxaborolane was added under a temperature −78° C., and the mixture was stirred overnight at room temperature. The reaction was stopped by adding saturated aqueous sodium chloride, the mixture was then extracted with chloroform, dried with anhydrous sodium sulfate, and then the filtrate was collected after filtration and the solvent was rotary evaporated to obtain the crude product. The crude product was purified by silica gel column chromatography using petroleum ether/ethyl acetate (15/1) as eluent to obtain the product.

In the step S02, the catalyst may be trifluoroacetic acid or its analogs, the oxidant may be dichloro-dicyano-benzoquinone (DDQ) or its analogues, which is not limited. The solvent may be dichloromethane, tetrahydrofuran, carbon tetrachloride, chloroform or acetonitrile, etc. The reaction equation was as follows:

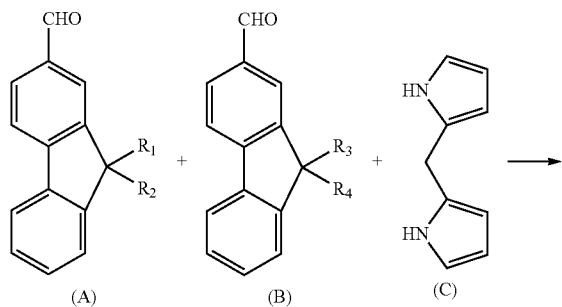

In detail, an anhydrous oxygen-free device was firstly established, compounds A, B, and C were weighted (e.g. according to molar ratio of 1/1/2) and dissolved in dichloromethane, nitrogen was inlet, and trifluoroacetic acid was added along with stirring. Two molar equivalent of dichloro-dicyano-benzoquinone (DDQ) was added, continue stirring, and triethylamine was added to carry out a quenching reaction. The solvent was concentrated, filtrated, the filtrate was collected and solvent was spin dried. The filtrate was then purified by silica gel column chromatography using dichloromethane as eluent, solvent was spin dried, the product, namely fluorenyl porphyrin compounds, was obtained by recrystallization with diethyl ether/methanol.

In step 03, the solvent may be but not limited to chloroform or tetrahydrofuran, etc. In detail, fluorenyl porphyrin compounds (e.g. 5,15-bis (9,9-dialkyl-fluorenyl)porphyrin) was dissolved in chloroform, a few amount of pyridine is added. The reactants is cooled to 0° C., the amount of N-bromo succinimide is added, after stirring, the mixture is returned to room temperature, then continue stirring for several hours. The reaction is stopped by adding acetone, the solvent was removed, and the product is obtained by recrystallization with diethyl ether/methanol. The reaction equation was as follows:

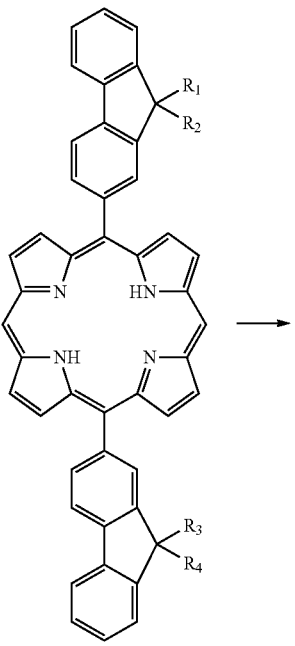

alkali metal carbonate, for example, but not limited to, solution of sodium hydroxide, potassium hydroxide solution, sodium carbonate solution, potassium carbonate solution, etc., preferably, sodium carbonate solution. The organic alkali solution may be aqueous solutions of alkyl hydroxide, ammonium hydroxide solution, for example, but not limited to, tetramethyl ammonium hydroxide, tetraethyl ammonium hydroxide, tetrapropylammonium hydroxide, ammonium, tetrabutyl ammonium hydroxide. The amount of the alkaline solution may be 5~20 times of the molar amount of the compound D. The solvent is a weak-polar aprotic organic solvent or a polar aprotic organic solvent or their mixtures, for example, but not limited to chloroform, methylene chloride, ethylene glycol dimethyl ether, dimethyl sulfoxide (DMSO), tetrahydrofuran (THF), toluene, xylene, or similar compounds, preferably toluene. The amount of the solvent is sufficient to make sure the various reactants are dissolved and adequate responsed.

The reaction in step S04 is illustrated in the following scheme:

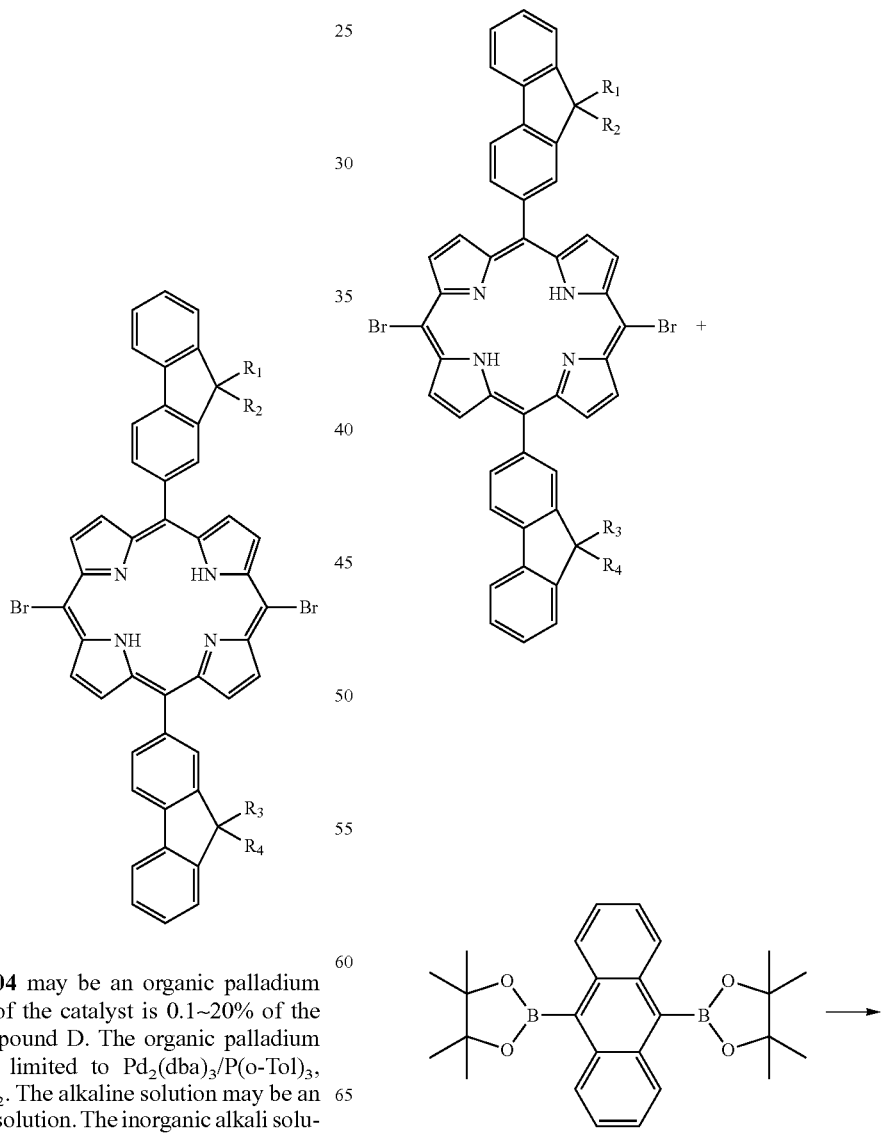

The catalyst in Step S04 may be an organic palladium catalyst, and the amount of the catalyst is 0.1~20% of the molar amount of the compound D. The organic palladium catalyst may be but not limited to $Pd_2(dba)_3/P(o\text{-}Tol)_3$, $Pd(PPh_3)_4$ or $Pd(PPh_3)_2Cl_2$. The alkaline solution may be an inorganic or organic alkali solution. The inorganic alkali solution may be aqueous solutions of alkali metal hydroxide or

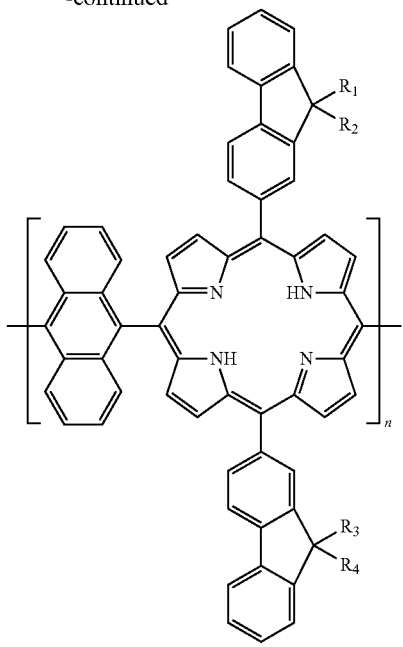

In detail, 1.0 mmol 1,4-bis(4,4,5,5-tetramethyl-1,3,2-dioxaborolane) based anthracene, 1.0 mmol 5,15-dibromo-10,20-bis(9,9-alkyl-fluorenyl)porphyrin, 0.01 mmol tetratis(triphenylphosphine)palladium, 3 ml of $Na_2CO_3$ aqueous solutions (2 mol/L), and 20 ml toluene were added to a round bottom flask. The flask was vacuum pumped to remove the oxygen and filled with nitrogen. The solution was heated to 50~120° C. for 12-80 hours. After the reaction, and the product was purified according to the following steps. The reaction product was poured into methanol, filtered in a Buchner funnel to separate the precipitate. The precipitate was rinsed with dilute HCl and then rinsed with acetone in a Soxhlet extractor for 12-72 hours to remove the monomer and catalyst residues, the remaining aggregate were dissolved in THF and chloroform to obtain the copolymer. The n in the copolymer is preferably 5~50, more preferably 10~30. In the actual preparation process, the desired degree of polymerization can be obtained by the choice of solvent, reaction temperature, reaction time, the amount of reactant, catalyst type and amount.

In the preparation method described above, the synthesis routes of three monomer A, B, and C are relatively simple and mature, which are basically one step synthesis, thereby reducing the manufacturing costs. In addition, bromide substitution reaction and Suzuki polymerization reaction are mature polymerization of high yield and under mild conditions, easy to control, and the solubility and molecular weight of the product is increased by the introduction of alkyl, such that a spin-coated polymer is realized.

The copolymer containing fluorenylporphyrin-anthracene according to the embodiment can be applied to a variety of electro-optical or semiconductor devices, such as solar cell devices, organic field-effect transistors, organic electroluminescent devices, organic optical storage devices, organic non-linear materials or organic laser devices. In the following description, solar cell devices, organic field-effect transistors, organic electroluminescent devices are taken as examples. Other devices, such as organic optical storage devices, organic nonlinear materials or organic laser devices have a similar structure, which use copolymer containing fluorenylporphyrin-anthracene according to the embodiment as optical storage materials, non-linear materials, laser materials or semiconductor materials.

Figure 3:
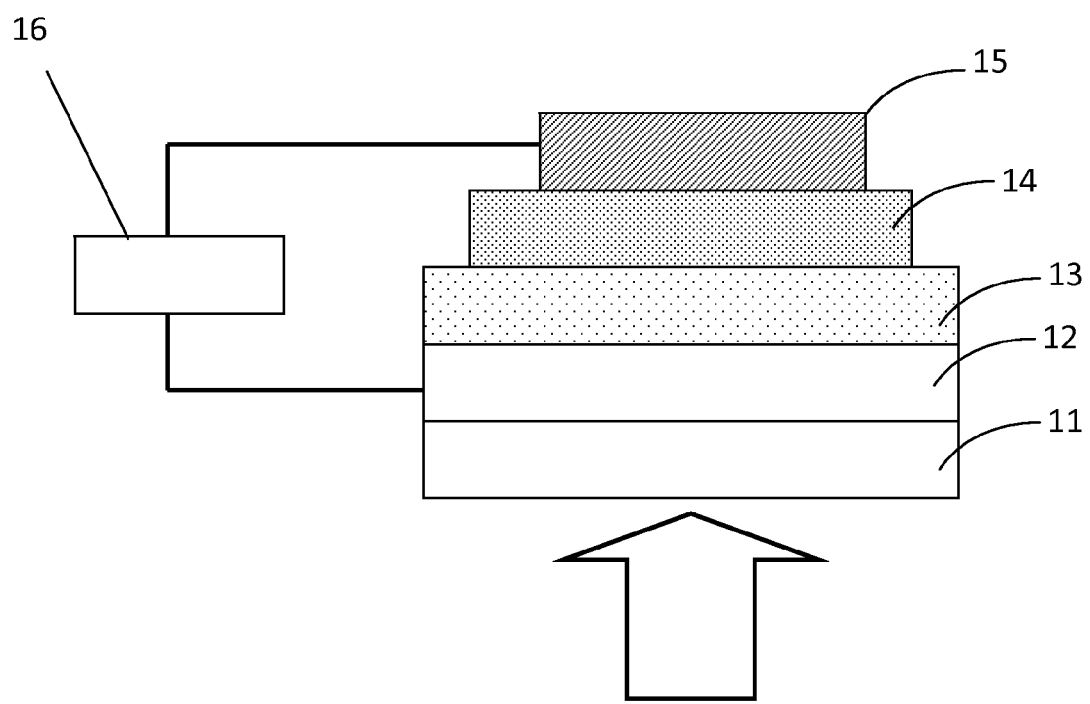
FIG. 3 is an embodiment of a solar cell device using a copolymer containing fluorenylporphyrin-anthracene.

Referring to FIG. 3, a solar cell device containing the copolymer containing fluorenylporphyrin-anthracene includes a glass substrate 11, a transparent anode 12, a middle auxiliary layer 13, an active layer 14, and a cathode 15, which are laminated in this order. The middle auxiliary layer 13 is made of a composite material of Poly(3,4-ethylenedioxythiophene): poly(styrenesulfonate) (PEDOT:PSS). The active layer 14 includes electron donor and electron acceptor materials; the electron donor material is the copolymer containing fluorenylporphyrin-anthracene; the electron acceptor material may be [6,6]-phenyl-C61-butyric acid methyl ester (PCBM). The transparent anode 12 may be indium tin oxide (ITO), preferably ITO having a sheet resistance of 10~20Ω/□. The cathode 15 may be aluminum electrodes or two-metal layer electrode, such as Ca/Al or Ba/Al layer electrode. In preparation, the glass substrate 11 may be the base, an ITO glass was selected and ultrasonic cleaned, and then oxygen-plasma treated. The middle auxiliary layer 13 was coated on the ITO glass, then the copolymer containing fluorenylporphyrin-anthracene and the electron acceptor material were mixed and coated on the middle auxiliary layer 13 to form the active layer 14. Next, the cathode 15 was deposited on the active layer 14 by vacuum evaporation technology, and the solar cell device was obtained. In one embodiment, the thickness of the transparent anode 12, the middle auxiliary layer 13, the active layer 14, and Ca/Al layer electrode are 160 nm, 40 nm, 150 nm, 20 nm, and 70 nm, respectively.

As illustrated in FIG. 3, when the solar cell device is irradiated, the light goes through the glass substrate 11 and the ITO electrode 12, the copolymer containing fluorenylporphyrin-anthracene in the active layer 14 absorbs solar energy and forms exciton. The exciton will be migrated to the interface between the electron donor materials and the electron acceptor materials, and electrons are transferred to the electron acceptor material, such as PCBM, such that the separation of the charge is realized, and the free carriers, i.e. free electrons and holes, are formed. The free electrons are passed to the metal cathode along the electron acceptor material and are collected by the cathode; the free holes is passed to the ITO anode along the electron donor materials and is collected by the anode, such that the photocurrent and photovoltage are formed and photoelectric conversion is achieved. When the solar cell device is connected to a load 16, the solar cell device may supply power to the load 16. During the process, because of wide spectral response range of the copolymer containing fluorenylporphyrin-anthracene, solar energy can be more fully used in order to obtain a higher photoelectric conversion efficiency, and increase the capacity of the electricity production of solar cell devices. Furthermore, this type of organic material can reduce the weight of solar cell devices, and can be produced by technologies such as spin coating, thus facilitating the large-scale production.

Figure 4:
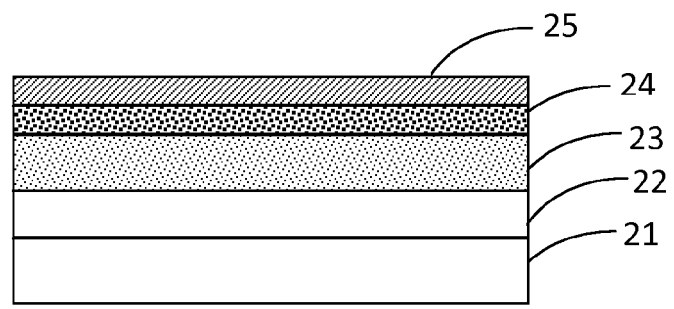
FIG. 4 is an embodiment of an organic electroluminescent device using a copolymer containing fluorenylporphyrin-anthracene.

Referring to FIG. 4, an organic electroluminescent device containing the copolymer containing fluorenylporphyrin-anthracene includes a glass substrate 21, a transparent anode 22, a light-emitting layer 23, a buffer layer 24, and a cathode 25, which are laminated in this order. The transparent anode 22 may be indium tin oxide (ITO), preferably ITO having a sheet resistance of 10~20Ω/□. The light-emitting layer 23 contains the copolymer containing fluorenylporphyrin-anthracene. The buffer layer 24 may be made of, but not limited to LiF, etc. The cathode 25 may be but not limited to aluminum electrodes or barium electrode. Therefore, in a specific embodiment, the organic electroluminescent device can be represented by ITO/copolymer containing fluorenylporphyrin-anthracene/LiF/Al. The various layers described above can be formed by conventional methods, and the copolymer containing fluorenylporphyrin-anthracene can be spin coated on the ITO.

Figure 5:
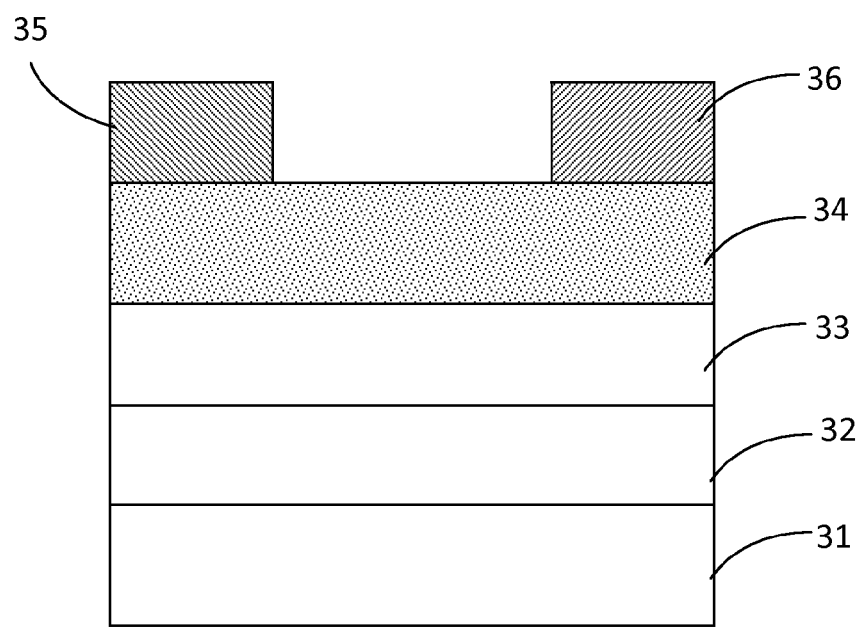
FIG. 5 is an embodiment of an organic field-effect transistor using a copolymer containing fluorenylporphyrin-anthracene.

Referring to FIG. 5, an organic field-effect transistor containing the copolymer containing fluorenylporphyrin-anthracene includes a substrate 31, an insulation layer 32, a modified layer 33, an organic semiconductor layer 34, which are laminated in this order, and a source electrode 35 and a drain electrode 36 formed on the organic semiconductor layer 34. The substrate 31 may be, but not limited to high-doped silicon (Si); the insulation layer 32 may be, but not limited to $SiO_2$ having a micro-nm (e.g. 450 nm) thickness. The organic semiconductor layer 34 may be the copolymer containing fluorenylporphyrin-anthracene. The source electrode 35 and the drain electrode 36 are made of, but not limited to gold. The modified layer 33 may be but not limited to octadecyltrichlorosilane. The substrate 31, the insulation layer 32, the modified layer 33, the source electrode 35, and the drain electrode 36 can be formed by conventional methods. The organic semiconductor layer 34 may be formed by spin coating the copolymer containing fluorenylporphyrin-anthracene to the insulation layer 32 modified by the modified layer 33.

The following examples are provided for illustrate certain aspects of the preparation method of the copolymer containing fluorenylporphyrin-anthracene and its performance. The compounds A, B, C, and D in the embodiment can be prepared accordingly or can also be purchased directly from the market.

Step 1, 5,15-(9,9-dialkyl-fluorenyl)porphyrin was prepared according to the following steps: an anhydrous oxygen-free device was firstly established, compounds A, B, and C were weighted according to molar ratio of 1:1:2 and dissolved in dichloromethane, in which the compounds A and B have the same structure as 9,9-bis(hexyl)-(hexyl)-2-formylfluorene; the compound C is dipyrrole methane. The nitrogen was inlet, and trifluoroacetic acid was added, the mixture was stirred for 3 hours at room temperature. Then two molar equivalent of dichloro-dicyano-benzoquinone (DDQ) was added, continue stirring for 30 minutes at room temperature, and triethylamine was added to carry out a quenching reaction. The solvent was concentrated, filtrated, the filtrate was collected and solvent was spin dried. The filtrate was then purified by silica gel column chromatography using dichloromethane as eluent, solvent was spin dried, the product was obtained by recrystallization with diethyl ether/methanol.

Step 2, preparation of the 5,15-dibromo-10,20-bis(9,9-hexyl-fluorenyl)porphyrin 5,15-bis(9,9-hexyl-fluorenyl)porphyrin was dissolved in chloroform, a small amount of pyridine was added. When the temperature of the reactants dropped to 0° C., an appropriate amount of N-bromo succinimide was added, the mixture was stirred for 0.5 hours and recovered to room temperature. The mixture was then continue stirred for 4 hours and the reaction was terminated by adding acetone, the solvent was removed and the product is obtained by recrystallization with diethyl ether/methanol.

Step 3, preparation of the copolymer containing fluorenylporphyrin-anthracene. In this embodiment, the copolymer containing fluorenylporphyrin-anthracene is represented by formula below:

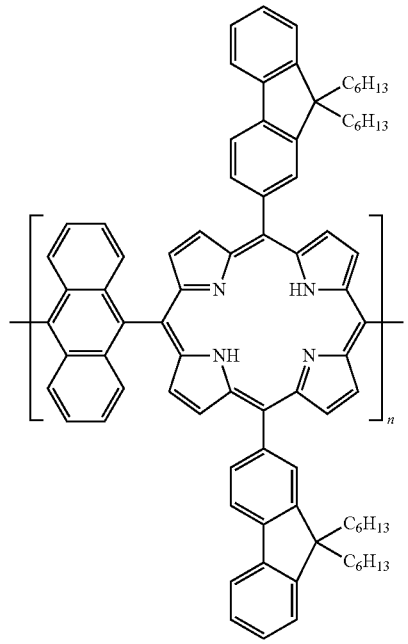

In detail, 1,4-bis(4,4,5,5-tetramethyl-1,3,2-dioxaborolane) based anthracene, 5,15-dibromo-10,20-bis(9,9-alkyl-fluorenyl)porphyrin, tetrakis (triphenylphosphine)palladium, $Na_2CO_3$ aqueous solutions, and toluene were added to a round bottom flask. The flask was vacuum pumped to remove the oxygen and filled with nitrogen. The solution was firstly refluxed for 48 hours in $N_2$ atmosphere, and then poured into methanol, filtered in a Buchner funnel to separate the precipitate. The precipitate was rinsed with dilute HCl and then rinsed with acetone in a Soxhlet extractor for 24 hours to remove the monomer and catalyst residues, the remaining aggregate were dissolved in THF and chloroform to obtain the copolymer with the yield was 32%.

In the copolymer containing fluorenylporphyrin-anthracene described above, the fluorene or fluorene derivatives have excellent light stability and thermal stability, and have structures for easy modification. Heterocyclic multi-aromatic ring or aromatic heterocyclic molecules can be introduced to increase the density of the skeletal electron cloud of the copolymer containing fluorenylporphyrin-anthracene, so as to narrow the copolymer bandgap. Porphyrin structure can make the copolymer appear a high quantum efficiency of the charge transfer and energy transfer reactions, and an excellent electronic buffer and photoelectromagnetism, a good rigid-flexibility, a better thermal stability and environmental stability. Anthracene has a good stability and good film-forming ability, too, it also possesses a better carrier transport characteristic. Anthracene has a high hole mobility, such that the carrier transport properties and the carrier transport characteristic of the copolymer containing fluorenylporphyrin-anthracene can be improved. When the copolymer containing fluorenylporphyrin-anthracene is applied to solar cell devices, organic field-effect transistors, organic electroluminescent devices, organic optical storage devices, organic non-linear materials or organic laser devices, the optical or semiconductor-related performance can be improved, and it can reduce the weight of the device, and thus facilitating the large quantities preparation.

Although the invention has been described in language specific to structural features and/or methodological acts, it is to be understood that the invention defined in the appended claims is not necessarily limited to the specific features or acts described. Rather, the specific features and acts are disclosed as sample forms of implementing the claimed invention.

What is claimed is:

1. A copolymer containing fluorenylporphyrin-anthracene, comprising a polymer represented by formula (1):

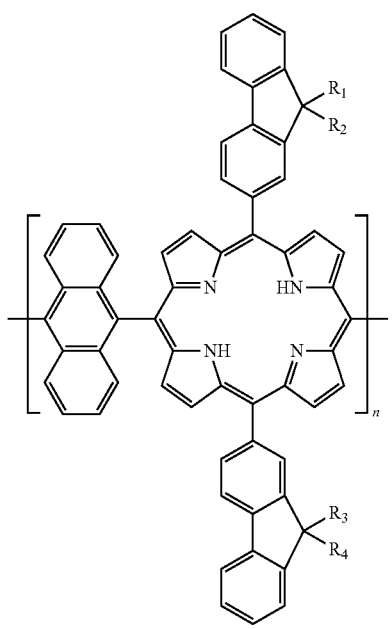

(1)

wherein $R_1$, $R_2$, $R_3$ and $R_4$, which may be identical or different, are $C_1$-$C_{16}$ alkyl, and n is an integer of 1 to 100.

2. The copolymer containing fluorenylporphyrin-anthracene according to claim 1, wherein $R_1$ and $R_3$ are identical $C_1$-$C_{16}$ alkyl; $R_2$ and $R_4$ are identical $C_1$-$C_{16}$ alkyl.

3. The copolymer containing fluorenylporphyrin-anthracene according to claim 1, wherein $R_1$, $R_2$, $R_3$, and $R_4$ are identical $C_1$-$C_{16}$ alkyl.

4. The copolymer containing fluorenylporphyrin-anthracene according to claim 1, wherein n is an integer of 5 to 50.

5. A preparation method of a copolymer containing fluorenylporphyrin-anthracene, comprising the steps of: providing compounds A, B, C, and D represented by formulas:

A:

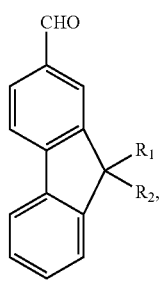

B:

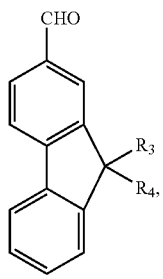

C:

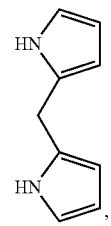

D:

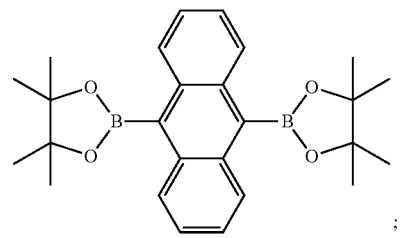

wherein $R_1$, $R_2$, $R_3$ and $R_4$, which may be identical or different, are $C_1$-$C_{16}$ alkyl; performing polycondensation oxidation reaction with compounds A, B, and C in a system containing a solvent, a catalyst and an oxidant to produce a fluorenyl porphyrin compound; performing bromide substitution reaction with the fluorenyl porphyrin compound in a system containing a solvent and a catalyst to produce a dibromo substituted fluorenyl porphyrin compound; and Suzuki polymerizing the dibromo substituted fluorenyl porphyrin compound and the compound D in the presence of a catalyst, a solvent and an alkaline solution to produce a polymer represented by formula (I):

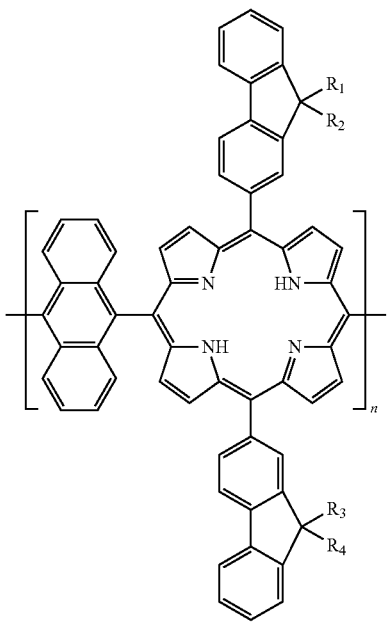

(1)

wherein n is an integer of 1 to 100.

6. The preparation method according to claim 5, wherein the catalyst used in the polycondensation oxidation reaction is trifluoroacetic acid; and the oxidant used in the polycondensation oxidation reaction is dichloro-dicyano-benzoquinone.

7. The preparation method according to claim 5, wherein the catalyst used in the Suzuki polymerizing reaction is an organic palladium catalyst; and the alkaline solution used in the Suzuki polymerizing reaction is an inorganic alkaline aqueous solution or an organic alkaline aqueous solution, the solvent used in the Suzuki polymerizing reaction is a weak-polar aprotic organic solvent or a polar aprotic organic solvent or mixtures thereof.

8. The preparation method according to claim 5, wherein the catalyst used in the bromide substitution reaction is pyridine, pyridine derivatives, or triethylamine; and the solvent is chloroform or tetrahydrofuran.

9. The preparation method according to claim 5, further comprising a purification step after the Suzuki polymerizing reaction, comprising: pouring a product of the Suzuki polymerizing reaction into methanol; filtering and separating a precipitate; rinsing the precipitate; rinsing the obtained solid using acetone in a Soxhlet extractor to remove monomer and catalyst residues, and obtaining the copolymer containing fluorenylporphyrin-anthracene.

10. An organic solid state device including a copolymer containing fluorenylporphyrin-anthracene according to claim 1 wherein said organic solid state device is one of a solid state devices selected from the group of a solar cell device, organic field-effect transistor, organic electroluminescent device, organic optical storage device, organic nonlinear material or organic laser device.

11. An organic solid state device including a copolymer containing fluorenylporphyrin-anthracene according to claim 2 wherein said organic solid state device is one of a solid state devices selected from the group of a solar cell device, organic field-effect transistor, organic electroluminescent device, organic optical storage device, organic nonlinear material or organic laser device.

12. An organic solid state device including a copolymer containing fluorenylporphyrin-anthracene according to claim 3 wherein said organic solid state device is one of a solid state devices selected from the group of a solar cell device, organic field-effect transistor, organic electroluminescent device, organic optical storage device, organic nonlinear material or organic laser device.

13. An organic solid state device including a copolymer containing fluorenylporphyrin-anthracene according to claim 4 wherein said organic solid state device is one of a solid state devices selected from the group of a solar cell device, organic field-effect transistor, organic electroluminescent device, organic optical storage device, organic nonlinear material or organic laser device.

* * * * *